United States Patent [19]

Young

[11] 4,281,932

[45] Aug. 4, 1981

[54] LIGHT ABSORPTIVITY MEASURING DEVICE

[76] Inventor: Thomas A. Young, Box 1018, Oak Hill, W. Va. 25901

[21] Appl. No.: 48,658

[22] Filed: Jun. 14, 1979

[51] Int. Cl.³ .............................................. G01J 3/50
[52] U.S. Cl. .................................... 356/416; 356/433; 356/425; 356/448
[58] Field of Search ................. 356/51, 408, 416, 433, 356/434, 425, 448

[56] References Cited
U.S. PATENT DOCUMENTS 3,661,462  5/1972  Natens ..................................... 356/51

Primary Examiner—F. L. Evans

[57] ABSTRACT

A light source is arranged with a light sensing device in such a way that the sensing device receives transmitted light for a translucent medium or reflected light for an opaque medium. The reading of the sensor is stored, then the same source and sensing device are moved over a reference medium whose absorptivity varies unidirectionally. A comparator compares the reading of the sensor with the stored reading and indicates when they are equal. The relative position of the reference and sensor indicates the absorptivity of the medium. One embodiment uses multiple devices and filters to determine composite color.

3 Claims, 8 Drawing Figures

LIGHT ABSORPTIVITY MEASURING DEVICE

This invention relates to the quantative measurement of the light absorptivity characteristics of a medium, and more particularly to a means for measuring absorptivity by comparing the absorptivity of the medium to be measured with that of a reference medium of varying absorptivity.

Previous methods of measuring light reflectivity or transmissivity have employed various techniques to reduce the effect of drift and non-linearity of the light sources and sensors. These techniques have ranged from the use of reference light sources and sensors to the use of a reference medium to determine a specific absorptivity. These methods have had the difficulties of either being limited by the repeatability or matching of devices, or of not having the ability to determine absorptivity over a continuous range.

These difficulties are overcome by the present invention, which allows measurement of the light absorptivity of a medium over a continuous range using a single light source and sensor for each color, without dependence on the long term stability or linearity of these devices. This is accomplished by using a reference medium, whose light absorptivity varies along some dimension over the range to be measured. In use, the light source-sensor combination is subjected to the medium to be tested, and the reading is stored; for instance, the voltage of the sensor as charge on a capacitor. The source-sensor combination is then moved across the reference medium, while a comparator compares the stored reading with the sensor output. When the source-sensor combination passes the part of the reference medium with the same absorptivity as the medium under test, the comparator causes an indication; for instance, a tone, a light, or an electrical signal. The position of the source-sensor combination at this indication is the measure of the light absorptivity of the medium under test. This position may be indicated by a visual scale, a tactile scale for the blind, or a secondary conversion means, such as a potentiometer. The device, as described, can be used to determine the reflectivity of an opaque medium, such as reagent test paper, or the transmissivity of a translucent medium, such as film or reagent liquid. The device may be used successively with different filters, or multiple such devices properly filtered may be used, to determine the absorptivity of the test medium at different colors, and thereby to determine color characteristics.

The primary object of the invention is to provide an improved absorptivity measuring device in which the measurement is independent of the characteristics of the light source and sensor.

It is a further object of the invention to provide a means for measuring reflectivity or transmissivity in which the output is a mechanical position.

It is a further object of the invention to provide an improved means for measuring the color or color characteristics of a medium.

Figure 1:
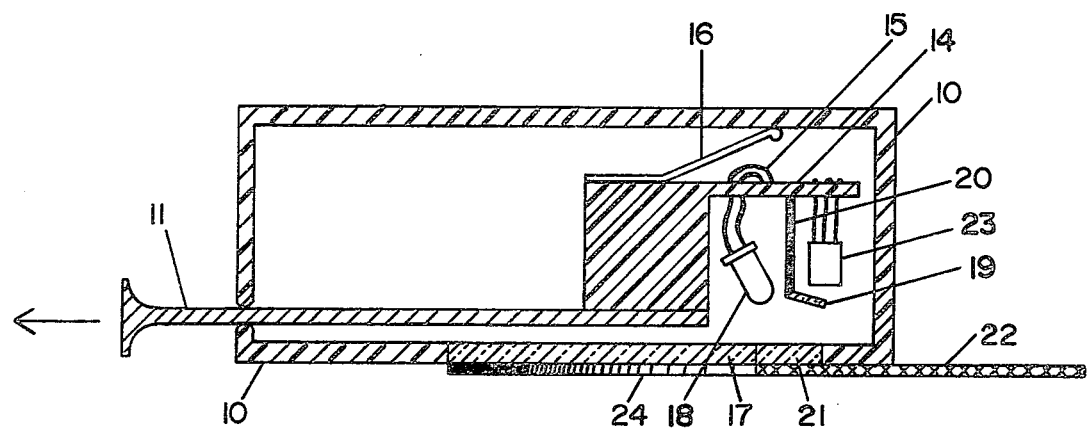
FIG. 1 is a section view of an embodiment of the invention for measuring reflectivity.
Figure 2:
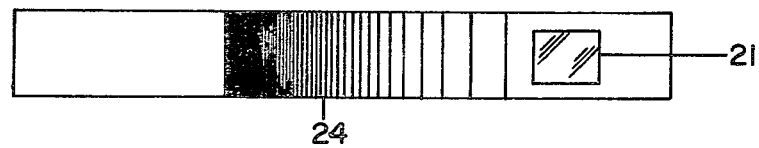
FIG. 2 is a top view of the reference strip and window which form the base of FIG. 1.
Figure 3:
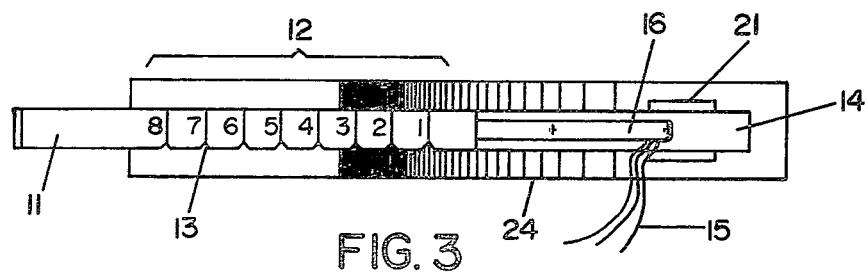
FIG. 3 is a top view with the slide in place showing calibration marks on the slide.

Referring to the drawings, FIGS. 1, 2, and 3 show relevant views of one embodiment of the invention. This embodiment comprises a light-tight housing 10 in which an indicating slide assembly 11 is mounted. The slide assembly comprises an indicating scale 12 including notches 13 for tactile indication of reflectivity, a read-head 14, flexible wires 15 leading to the circuitry, and a spring 16 to keep the read-head a constant distance from the working surface 17.

The read-head consists of a light source 18 arranged with a filter 19 and a baffle 20 in such a way that light from the source passes through the window 21, is reflected by the medium under test 22, and impinges on the light sensor 23. The working surface 17 (see FIG. 2) consists of a window 21 and a reference reflectivity surface 24 which varies in reflectivity along the direction of travel of the slide 11. In use, the test medium is placed under the read-head with the slide in the position shown. The output of the sensor 23 is stored electronically as will be described later. The slide 11 is then pulled out in the direction shown by the arrow in FIG. 1. A comparator, to be described later, compares the output of the sensor 23 with the stored reading, while the slide is moved. When the read-head 14 passes the area on the reference 24 equal to the reflectivity of the test medium 22, the comparator changes polarity, driving a tone generator. The user then counts the number of exposed notches 13 to determine reflectivity.

Figure 4:
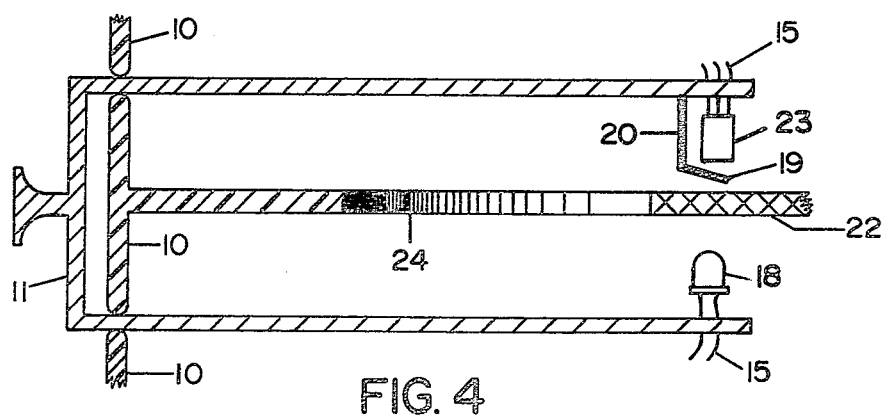
FIG. 4 is a section view of an arrangement for measuring transmissivity.

FIG. 4 shows a similar embodiment, except arranged to measure the transmissivity of a translucent medium. The parts are numbered functionally equivalent to those in FIGS. 1, 2, and 3. In this embodiment, the light passes from the light source 18, through the test medium 22, then through the filter 19, and is received by the sensor 23. The reference 24 is like that described above, except varying in transmissivity rather than reflectivity. The operation is as described above.

Figure 5:
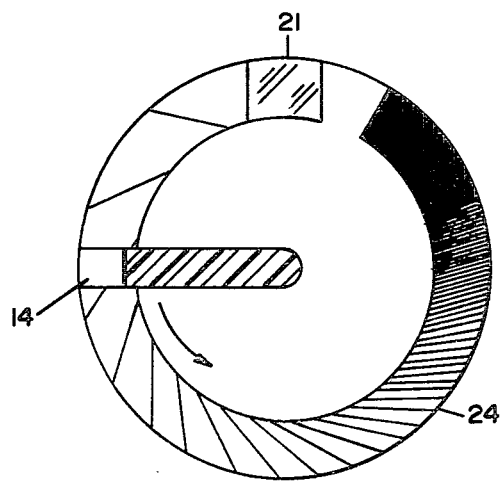
FIG. 5 is a top view of the invention arranged in rotational form.

FIG. 5 shows an equivalent system except arranged for rotational rather than linear output. The indication in this case is rotational position when the tone is heard.

Figure 6:
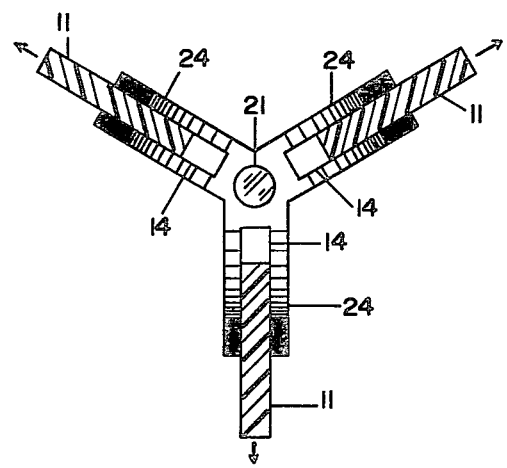
FIG. 6 is an arrangement for measuring absorptivity in three colors.

FIG. 6 shows three units as shown in FIG. 1, arranged to determine reflectivity at three primary colors. Each slide 11 has filter, arranged as 19 in FIG. 1, corresponding to a primary color. In use, the slides are operated successively to determine reflectivity at each primary color.

Figure 7:
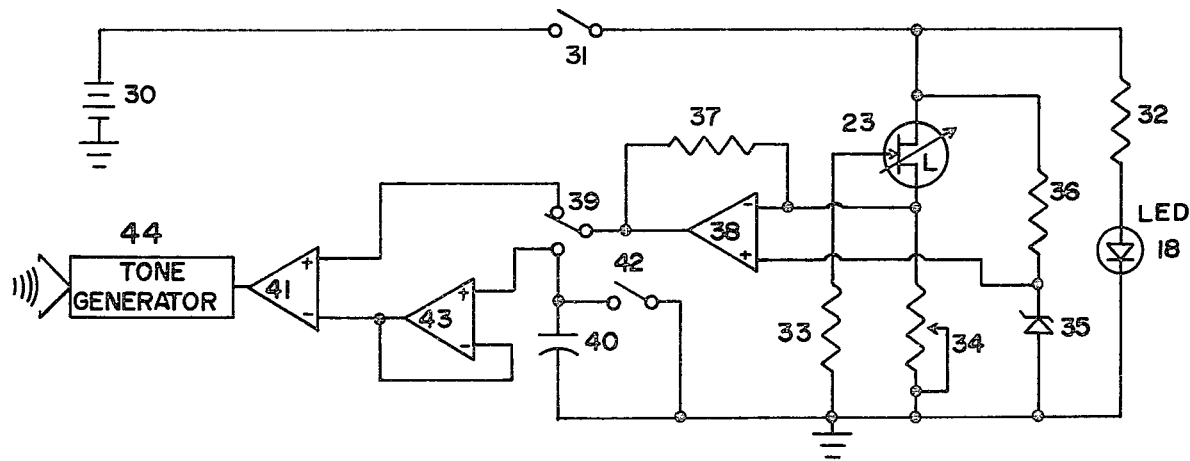
FIG. 7 is an electrical diagram of a circuit used to accomplish one embodiment of the invention.
Figure 8:
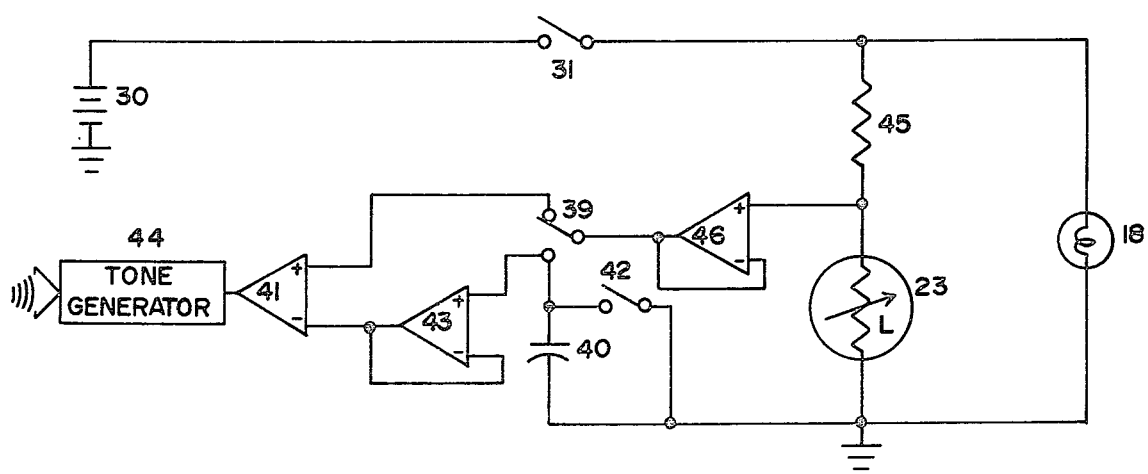
FIG. 8 is an electrical diagram of an alternative circuit.

FIGS. 7 and 8 show two circuits used to accomplish the storage and comparison described earlier.

FIG. 7 uses a battery 30 connected through a power switch 31 as a power supply. A dropping resistor 32 is connected to light emitting diode light source 18. A photo-field-effect transistor 23 is used as the light sensor. A gate resistor 33 and variable resistor 34 are used to set the transistor bias for the desired operating range. A zener diode 35 and dropping resistor 36 form a voltage reference. An operational amplifier 38 with feedback resistor 37 is used to amplify the change in transistor current caused by light. The output of this amplifier is connected by a single-pole double-throw switch 39 either to the storage capacitor 40 or the comparator 41.

Shorting switch 42 is used to discharge the storage capacitor 40 before a new reading is taken for a test sample. The voltage follower 43 is used to keep the storage capacitor 40 from discharging during comparison. In use, the storage capacitor 40 is discharged and switch 39 connects the output of amplifier 38 to the storage capacitor 40, while the read-head (14, FIG. 1) is positioned over the test sample (22, FIG. 1). This stores a voltage relating to the reflectivity of the sample on capacitor 40. Switch 39 is then moved to connect the output of amplifier 38 to comparator 41. The slide (11, FIG. 1) is then pulled out along the varying reference (24, FIG. 1). When the read-head (14, FIG. 1) passes the point on the reference strip of reflectivity equal to that of the test sample, the voltage from amplifier 38 exceeds that stored on capacitor 40 causing the comparator 41 to change polarity and driving tone generator 44. This causes an audible signal, and the position of the slide 11 indicates the reflectivity of the test sample.

FIG. 8 shows circuitry to accomplish the same function using an incandescent light source 18 and a photoresistor light sensor 23. The photoresistor 23 is biased by a fixed resistor 45, and follower 46 is used to unload the photo-resistor. From switch 39 on, the function and components are exactly as described for FIG. 7. Also, the operation is as described for FIG. 7.

What I claim is:

1. A device for measuring the light absorptivity characteristics of a medium over some substantially continuous range, comprising one or more absorptivity measuring devices, each consisting of a light source-sensor, a means for limiting the range of color response, a means for storing the sensor output representative of the medium under test, a reference consisting of a medium unidirectionally varying in absorptivity, a comparator to indicate equality of the sensor output representative of said reference and that output stored by said storing means, and a means for moving said light source-sensor combination over the medium under test and then over said reference medium using the same color range, the position on said reference medium relative to the light source-sensor combination when said comparator indicates equality being the measure of the absorptivity of said medium under test.

2. A device as described in claim 1, comprising one absorptivity measuring device as described in claim 1, for measurement of the absorptivity of a medium in one color range.

3. A device as described in claim 1, comprising two or more absorptivity measuring devices, each responsive to a different color range for measurement of the light absorptivity of the medium under test at more than one color.

* * * * *